United States Patent [19]
Kanai

[11] Patent Number: 5,590,665
[45] Date of Patent: Jan. 7, 1997

[54] METHOD OF DIAGNOSING CEREBRAL INFARCTION

[75] Inventor: Kazuyuki Kanai, Kasai, Japan

[73] Assignee: Toa Medical Electronics Company, Ltd., Kobe, Japan

[21] Appl. No.: 338,826

[22] Filed: Nov. 10, 1994

Related U.S. Application Data

[63] Continuation of Ser. No. 997,537, Dec. 28, 1992, abandoned.

[30] Foreign Application Priority Data

Dec. 27, 1991 [JP] Japan .................... 3-358698

[51] Int. Cl.$^6$ .................................. A61B 19/00
[52] U.S. Cl. .................. 128/898; 364/413.02; 395/21
[58] Field of Search ............... 128/897–98; 364/413.01, 364/413.02; 395/21–23, 50–51

[56] References Cited

U.S. PATENT DOCUMENTS

| | | | |
|---|---|---|---|
| 4,875,183 | 10/1989 | Graf et al. | 364/807 |
| 4,876,731 | 10/1989 | Loris et al. | 382/40 |
| 5,218,529 | 6/1993 | Meyer et al. | 364/413.01 |

OTHER PUBLICATIONS

Editorial—"Neural Networks: What Are They?", Annals of Internal Medicine, vol. 115, No. 11, pp. 906–907, Dec. 1, 1991.
Baxt—"Use of an Artificial Neural Network . . . ", Annals of Internal Medicine, vol. 115, No. 11, pp. 843–848, Dec. 1991.
Scott, et al.—"Neural Network Analysis of . . . ", Radiology, vol. 186, No. 3, pp. 661–664, Recieved Aug. 3, 1992.
Saito, et al: "Medical Diagnostic Expert System Based on PDP Model", presented at IEEE Conference, Jul. 24–27, 1988, pp. I-255 to I-262.
Bounds, et al: "A Multi Layer Perception Network for the Diagnosis of Low Back Pain", IEEE Conference, Jul. 24–27, 1988, pp. II-481 to II-489.
Hecht-Nielsen: *Neurocomputing Applications: Sensor Processing, Control, and Data Analysis*, "The Instant Physician", pp. 354–356, ©1990, Addison–Wesley.
Akira Suehiro et al., "Clinical Usefulness of the Measurement of Plasma D-dimer Levels", The Japanese Journal of Clinical Pathology, vol. 39, No. 7, pp. 694–700, Jul. 1991.
"Clinical Significance of New Coagulation and Fibrinolytic Markers in Ischemic Stroke Patients", by Noriko Ono et al., STROKE vol. 22, No. 11, Nov. 1991, pp. 1369–1373.

*Primary Examiner*—Angela D. Sykes
*Assistant Examiner*—John P. Lacyk
*Attorney, Agent, or Firm*—Banner & Allegretti, Ltd.

[57] ABSTRACT

A novel method of diagnosing cerebral infarction using a neural network, wherein plural sets of data previously obtained from healthy and sick persons, each including an age, measured values of coagulo-fibrinolytic molecular markers ( e.g., D-dimer, TAT and PAP) , an index indicative of the state of cerebral infarction (e.g., 0 for healthy persons and 1 for sick persons) and the like, are repeatedly input into a neural network to let it learn the correlation of these characteristics and, thereafter, a set of data of a person to be diagnosed, including his age, measured values of the coagulo-fibrinolytic molecular markers and the like, are input in the neural network to obtain an index indicative of his state of cerebral infarction as a degree of dangerousness of cerebral infarction. This method is significantly higher in accuracy as compared with the prior art methods using the same data.

2 Claims, 2 Drawing Sheets ated filling factor = 5,590,665

METHOD OF DIAGNOSING CEREBRAL INFARCTION

This application is a continuation of application Ser. No. 07/997,537 filed in Dec. 28, 1992 and now abandoned.

This invention relates to a method of diagnosing cerebral infarction and, especially, to a novel and improved method of determining a degree of dangerousness of cerebral infarction using a neural network.

Cerebral infarction is referred to as such a state in that a cerebral artery clogs for some cause and impedes or stops blood flow in the downstream tissue. About 20% of the cause of death of mankind is cerebro-vascular disease and about 50% thereof is occupied by cerebral infarction. Cerebral infarction is classified into cerebral embolism and cerebral thrombosis. Cerebral embolism has no direct cause in the cerebral artery and becomes onset with coagulation of blood, albumin, fat or the like forming in the heart, by heart disease such as atrial fibrillation or cardiomyopathy, and flowing into the cerebral artery to clog the same. In contrast, cerebral thrombosis is caused by a vascular endothelium incrustated by arteriosclerosis of the cerebral artery. The frequency of onset is higher in cerebral thrombosis than in cerebral embolism.

In the present method of diagnosing arteriosclerosis which may be a cause of cerebral embolism, there are indirect method such as funduscopy, X-ray computed tomography, magnetic resonance imaging, pulse wave method or ultrasonic blood-flow measurement and direct method such as angiography, angio-endoscopy or angio-echo, though both of these indirect and direct methods are not satisfactory.

Recently, it has become possible to specifically measure values of coagulo-fibrinolytic molecular markers such as D-dimer or the like and, moreover, it has been found that these coagulo-fibrinolytic molecular markers have some relation to arteriosclerosis of the circulating system. For example, in the article of Suehiro et al. entitled "Clinical Usefulness of the Measurement of Plasma D-dimer Levels", The Japanese Journal of Clinical Pathology Society of Clinical Pathology, it is reported that the value of D-dimer, which is a coagulo-fibrinolytic molecular marker, is high in patients of cerebral infarction. The article also reported a positive correlation between the D-dimer value and age for each patient. Further, the values of thrombin-antithrombin III complex (hereinunder referred to as TAT) and plasmin $\alpha_2$ antiplasmin complex (hereinunder referred to as PAP) behave similarly.

Although this report suggests utility of the above-mentioned coagulo-fibrinolytic molecular marker values as an index of the state of cerebral infarction, it does not show any method of using the same to judge the state of cerebral infarction. It has been a general practice to use discriminant analysis or multiple regression analysis for calculating the degree of significance of linear relationship of such variations showing uncertain correlation or, in this case, the probability of ischemic stroke (hereinunder referred to as "dangerousness of cerebral infarction"). However, there is an unavoidable limit of accuracy in such basically linear method of discrimination.

Accordingly, an object of this invention is to provide a novel and improved method of diagnosing cerebral infarction which can effect highly sensitive and accurate discrimination using the above-mentioned well-known variables.

SUMMARY OF INVENTION

This object can be attained by the method according to this invention, which comprises the steps of repeatedly inputting plural sets of data to be learnt (teaching data sets) into a neural network to let the neural network learn the same, each set including an age, coagulo-fibrinolytic molecular marker measurements and an index indicative of cerebral infarction obtained from each of healthy persons and patients of cerebral infarction, and putting a set of data to be tested in the neural network (testing data set) to obtain the dangerousness of cerebral infarction of a person to be tested, the set of data including an age and coagulo-fibrinolytic molecular marker measurements obtained from the person to be tested.

The usable coagulo-fibrinolytic molecular markers are at least one of D-dimer, TAT and PAP and the set of data to be learnt teaching data and tested testing data may include a value of sex distinction.

Now, the features and operational effects of this invention will be described in more detail below in connection with preferred embodiments with reference to the accompanying drawings.

DESCRIPTION OF PREFERRED EMBODIMENTS

Figure 1:
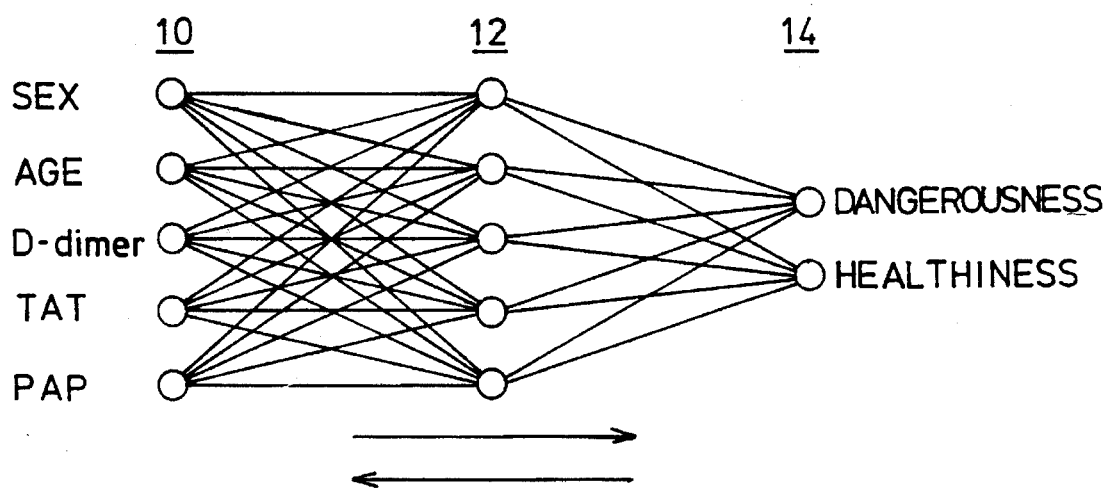
FIG. 1 is a schematic view showing a neural network used in the embodiments of the method of diagnosing cerebral infarction according to this invention.

Referring to FIG. 1, the neural network is one using error back-propagation algorithm and has a three-layer structure consisting of an input layer 10, an intermediate or hidden layer 12 and an output layer 14. The input layer 10 has five neurons corresponding to five input data respectively consisting of the values indicative of sex distinction, age, and measurements of three coagulo-fibrinolytic molecular markers such as D-dimer, TAT and PAP as described above. The three coagulo-fibrinolytic molecular marker measurements can be obtained by well-known methods and the values indicative of sex distinction and age are obtained as described below.

The output layers 14 has two neurons respectively corresponding to the values indicative of the degrees of healthiness and dangerousness regarding cerebral infarction (hereinunder referred to simply as "healthiness" and "dangerousness"). While the hidden layer 12 generally has three to ten neurons, this number is determined as five in the embodiments for the reason as described below. Therefore, the neural network has twelve neurons in total in the following embodiments.

The five neurons in the input layer 10 have synaptic junctions with the give neurons in the hidden layer 12 and the five neurons in the hidden layer 12 have synaptic junctions with the two neurons in the output layer 14. Therefore, the total number of the synaptic junctions is thirty-five (35=5×5+5×2). Each synaptic junction has a weight with respect to its input signal and the weight is previously established in an initializing step.

Figure 2:
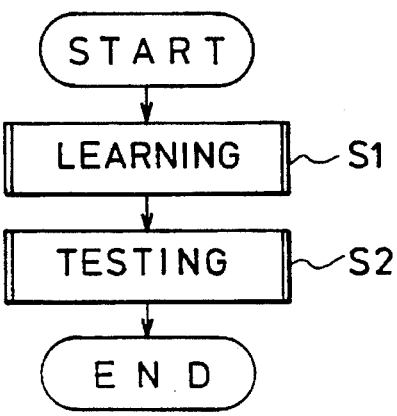
FIG. 2 is a flow chart showing a program for executing the method of the embodiment.

In the initialized neural network, a learning step S1 is executed first as shown in FIG. 2. In the learning step S1, the five kinds of input data are supplied to the input layer 10 as a set of learning inputs as described above, and the corresponding data of dangerousness and/or healthiness are supplied to the output layer 14 as teacher inputs. Then, the neural network calculates learning outputs of the dangerousness and/or healthiness from the learning inputs through the respective cynaptic junctions and compares them with the corresponding teacher inputs in the output layer 14. Next, the neural network turns back from the output layer 14 and calculates the internal states of the neurons of the respective layers toward the input layer 10 to correct the weights of the respective synaptic junctions so as to minimize the mean square errors between the learning inputs and the teacher inputs. This step is repeated for all sets of input data to finally determine the weights of the synaptic junctions. Thereafter, a testing step S2 is executed. In the testing step S2, data of the same items as the learning inputs obtained from a person to be tested are supplied to the input layer 10 to obtain the data of dangerousness and/or healthiness from the output layer 14.

The values of the input data to the neural network are not raw measured values of the respective characteristics but values from zero to one which are normalized in accordance with predetermined rules. In this embodiment, normalization was effected in accordance with the following rules.

(1) Sex distinction: Male=0 and Female=1.

(2) Age: Normalized age=Age (years)/100, where any age exceeding 100 years is assumed as 100 years.

(3) D-dimer: Normalized D-dimer value=D-dimer measurement (ng/ml)/500.0, where any measurement exceeding 500.0 ng/ml is assumed as 500.0 ng/ml.

(4) TAT: Normalized TAT value=TAT measurement (ng/ml)/16.0, where any measurement exceeding 16.0 ng/ml is assumed as 16.0 ng/ml.

(5) PAP: Normalized PAP value=PAP measurement (μg/ml )/1.5, where any measurement exceeding 1.6 μg/ml is assumed as 1.5 μg/ml.

(6) Dangerousness and healthiness: Maximum=1 and minimum=0.

The data for the learning inputs were obtained from 100 persons of cerebral infarction and 140 persons of non-cerebral infarction and the upper limits of D-dimer, TAT and PAP were determined with reference to their mean values plus twice their standard deviations.

Before commencing the learning step, it is necessary to determine the number of neurons in the hidden layer 12. If the number of neurons in the hidden layer 12 is small, no complexity of combination of the input data is transferred to the output layer 14. If it is too large on the contrary, the number of synaptic junctions increases to result in such disadvantages in that an excess time is needed for obtaining the output from the output layer 14 and the output value does not converge to its minimum value. The inventor used the above-mentioned learning input data to execute the learning step and evaluated the optimum number of neurons in the hidden layer 12 based upon the mean square error between the resultant output values of the respective neurons in the output layer 14 and the corresponding teacher input values, thereby obtaining five to seven. Thus, the number of neurons in the hidden layer 12 was determined as five in this embodiment.

Figure 3:
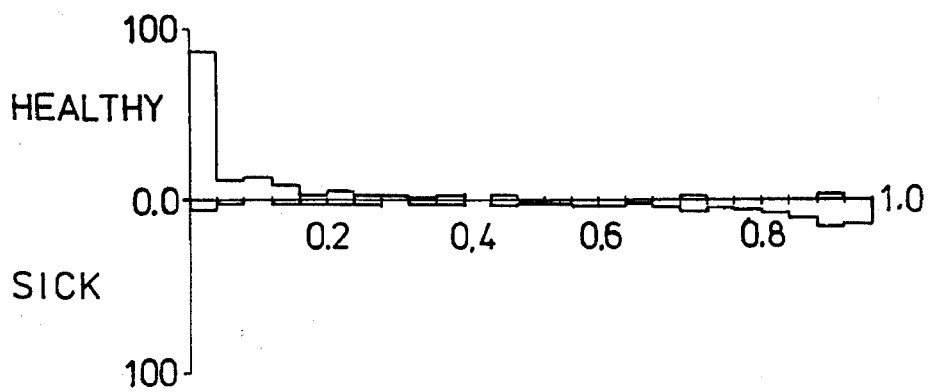
FIG. 3 is a histogram showing the result of diagnosis of cerebral infarction according to the embodiment.
Figure 4:
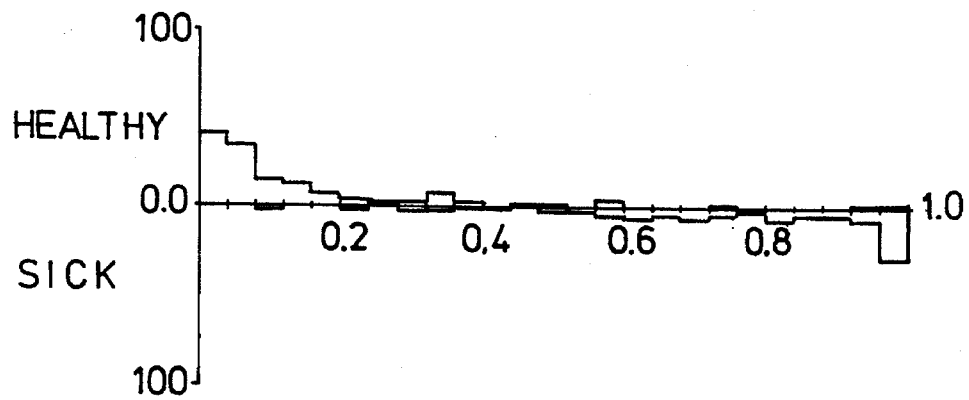
FIGS. 4 and 5 are histograms showing the results of diagnosis of cerebral infarction according to discriminant analysis and multiple regression analysis, respectively, for comparing with the result of FIG. 3.
Figure 5:
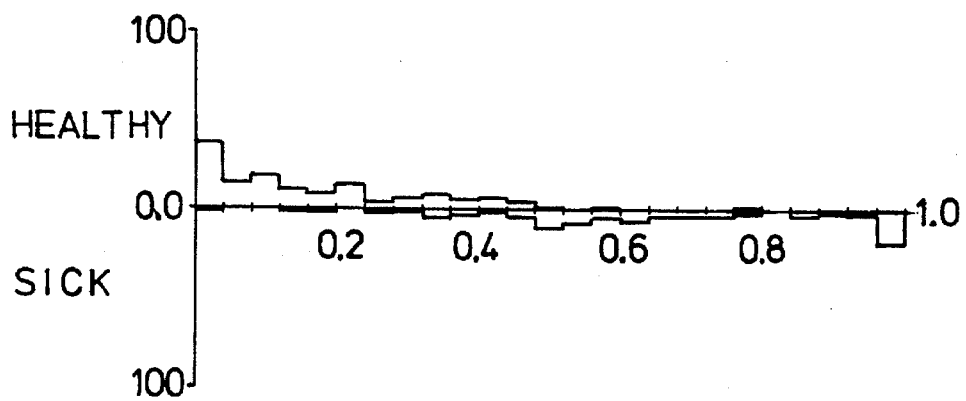

The distribution of dangerousness obtained from the data of the above-mentioned 240 persons to be tested is expressed as a histogram as shown in FIG. 3. FIGS. 4 and 5 show histograms of dangerousness distributions obtained from the same data by the above-mentioned discriminant analysis and multiple regression analysis, respectively. In the drawings, the abscissa shows the dangerousness of cerebral infarction and the ordinate shows the frequency (percent number) of persons of non-cerebral infarction (healthy persons) upwards and the frequency of persons of cerebral infarction (patients) downwards.

Figure 6:
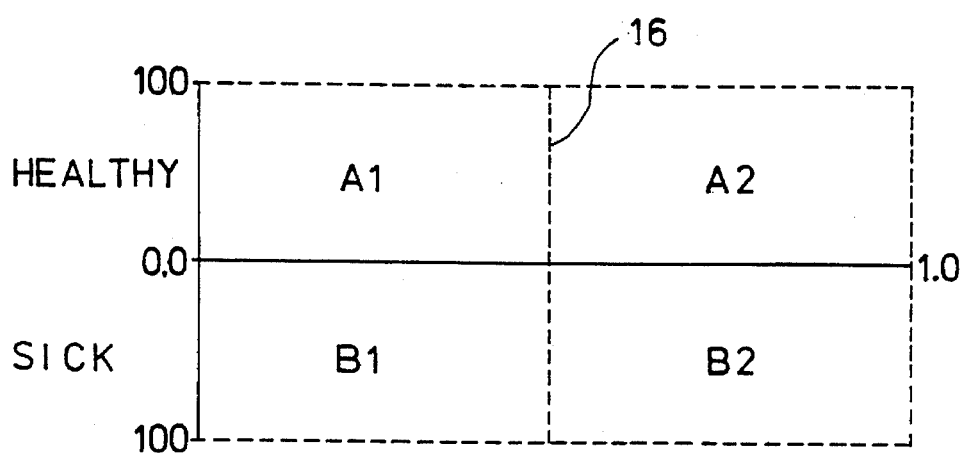
FIG. 6 is a diagram for explaining the histograms of FIGS. 3 to 5.

FIG. 6 shows a partition diagram used for diagnosing cerebral infarction of each tested person based upon these histograms. The diagram includes a rectangle having the abscissa and ordinate of the histograms as both sides and being divided into four sections by the abscissa and a split line 16. The upper left section A1 shows a true negative region for healthy persons, the upper right section A2 shows a false positive region for healthy persons, the lower left section B1 shows a false negative region for sick persons and the lower right section B2 shows a true positive region for sick persons. The accuracy of diagnosis varies with the horizontal position of the split line 16.

Next, sensitivity, specificity, false positive rate and false negative rate in diagnosis of cerebral infarction were sought using the histograms of FIGS. 3, 4 and 5 and the diagram of FIG. 6, where sensitivity meant percent chance of diagnosing patients of cerebral infarction as positive and specificity meant percent chance of diagnosing healthy persons as negative. The results obtained with the split line 16 drafted at 0.4, 0.5 and 0.6 of dangerousness are shown in Tables 1, 2 and 3, respectively.

TABLE 1

| | (Split line: 0.4) | | | |
|---|---|---|---|---|
| FIG. | Sensitivity | Specificity | False positive rate | False negative rate |
| 3 | 85.39% | 91.39% | 8.61% | 14.61% |
| 4 | 84.27% | 86.09% | 13.91% | 15.73% |
| 5 | 83.15% | 86.09% | 13.91% | 16.85% |

TABLE 2

| | (Split line: 0.5) | | | |
|---|---|---|---|---|
| FIG. | Sensitivity | Specificity | False positive rate | False negative rate |
| 3 | 83.15% | 94.04% | 5.96% | 16.85% |
| 4 | 83.15% | 90.73% | 9.27% | 16.85% |
| 5 | 69.66% | 95.36% | 4.64% | 30.34% |

TABLE 3

| | (Split line: 0.6) | | | |
|---|---|---|---|---|
| FIG. | Sensitivity | Specificity | False positive rate | False negative rate |
| 3 | 78.65% | 94.70% | 5.30% | 21.35% |
| 4 | 75.28% | 94.70% | 5.30% | 24.72% |
| 5 | 53.93% | 96.69% | 3.31% | 46.07% |

The followings can be said from the tables. (1) The inventive method and discriminant analysis have substantially same power when the split line is drafted at 0.5 of dangerousness. (2) In multiple regression analysis, its sensitivity drops extremely when the split line is drafted above 0.5 of dangerousness. (3) Sensitivity and specificity of the inventive method are high when the split line is drafted at 0.4 or 0.6 of dangerousness. Thus, it is found that there is less chance of presentation of medium degree of dangerousness in the inventive method and, therefore, it can result in sharp discrimination.

As a result of search for the false negative patients in the inventive method and discriminant analysis, it has been found that all of them are identical patients and the most of them are patients in acute period. Therefore, this false negativity might be caused by the difference of sick state between acute and chronic periods. Similarly, the false positive patients are other than those of disease of circulating system and some patients of hypertension are included therein. Since high blood pressure is a dangerous factor of arteriosclerosis, there would be no help for such diagnosis.

The above embodiment is presented only for the purpose of illustration and does not mean any limitation of the invention. It is a matter of course that various modifications and changes can be added thereto within the spirit and scope of the invention as defined in the apended claims. For example, the values of age and respective coagulo-fibrinolytic molecular markers were used as mutually independent input data in the above embodiment. In practice, however, it has been known that the values of coagulo-fibrinolytic molecular markers increase with age, or there is some relation between the coagulo-fibrinolytic molecular markers and age. However, it is desirable that the respective input data are independent of each other. Therefore, it is also possible to make the coagulo-fibrinolytic molecular markers independent of the age by previously seeking a standard value of each coagulo-fibrinolytic molecular marker of a healthy person at each age and supplying the standard value subtracted from each coagulo-fibrinolytic molecular marker measurement into the input layer 10 as the value of said coagulo-fibrinolytic molecular marker and it is expected that learning efficiency and diagnosing accuracy are thereby improved. While, in the above embodiment, sex distinction and three kinds of coagulo-fibrinolytic molecular markers, namely, D-dimer, TAT and PAP were used as the input data, it is enough to use at least one of the coagulo-fibrinolytic molecular markers together with the age. Moreover, a plurality of hidden layers may be used if necessary, though the hidden layer 12 was a single layer in the above embodiment.

I claim:

1. A method of diagnosing cerebral infarction, comprising the steps of:

obtaining a set of teaching data on each subject in a group of health subjects and subjects of cerebral infarction, each said teaching data set comprising an age of said subject, measurement of at least one coagulo-fibrinolytic molecular marker for said subject, and an index indicative of cerebral infarction for said subject;

modifying each said measurement of coagulo-fibrinolytic molecular marker in said teaching data in order to cause said measurements to be independent of age;

inputting each set of the modified teaching data into a neural network for use in diagnosing patients and making said neural network learn said teaching data;

obtaining a set of testing data on a patient to be diagnosed, said testing data comprising an age of said patient and measurement of said at least one coagulo-fibrinolytic molecular marker for said patient;

modifying each said measurement of coagulo-fibrinolytic molecular marker in said testing data in order to cause said measurements to be independent of age for purposes of said diagnosing;

inputting the modified testing data into said neural network and obtaining therefrom, as a diagnostic output for said patient, an index indicative of cerebral infarction which is specific to said patient; and diagnosing cerebral infarction in said patient from said index.

2. A method as in claim 1, and further comprising the steps of:

obtaining standard values, for each different age of said subjects and said patient, of each said coagulo-fibrinolytic molecular marker for a healthy person at each said different age; and modifying each said measurement, by removing a particular one of said standard values from each said measurement of each said coagulo-fibrinolytic molecular marker, for each said patient and subject having an age corresponding to said age for which said standard value was obtained.

* * * * *